United States Patent
Janusson et al.

(10) Patent No.: US 7,377,944 B2
(45) Date of Patent: May 27, 2008

(54) SOCKET LINER INCORPORATING SENSORS TO MONITOR AMPUTEE PROGRESS

(75) Inventors: Hilmar Br. Janusson, Seltjarnarnes (IS); Freygardur Thorsteinsson, Reykjavik (IS); Gudjon G. Karason, Sollentuna (SE)

(73) Assignee: OSSUR hf (IS)

( * ) Notice: Subject to any disclaimer, the term of this patent is extended or adjusted under 35 U.S.C. 154(b) by 0 days.

(21) Appl. No.: 10/615,336

(22) Filed: Jul. 8, 2003

(65) Prior Publication Data

US 2004/0059432 A1    Mar. 25, 2004

Related U.S. Application Data

(60) Provisional application No. 60/394,804, filed on Jul. 8, 2002.

(51) Int. Cl.
  *A61F 2/80* (2006.01)
(52) U.S. Cl. .......................................... 623/36
(58) Field of Classification Search .................. 623/36, 623/37, 33–34, 27, 57
  See application file for complete search history.

(56) References Cited

U.S. PATENT DOCUMENTS

| 3,949,388 | A | * | 4/1976 | Fuller ..................... 340/870.17 |
| 4,321,057 | A | * | 3/1982 | Buckles ...................... 435/7.1 |
| 4,494,950 | A |   | 1/1985 | Fischell |
| 4,895,574 | A |   | 1/1990 | Rosenberg |
| 5,054,488 | A | * | 10/1991 | Muz .......................... 600/344 |
| 5,222,506 | A | * | 6/1993 | Patrick et al. ............... 607/126 |
| 5,247,938 | A | * | 9/1993 | Silverstein et al. .......... 600/459 |
| 5,247,945 | A | * | 9/1993 | Heinze et al. ............... 607/129 |
| 5,253,656 | A |   | 10/1993 | Rincoe et al. |
| 5,258,037 | A | * | 11/1993 | Caspers ....................... 623/36 |
| 5,323,650 | A |   | 6/1994 | Fullen et al. |
| 5,408,873 | A | * | 4/1995 | Schmidt et al. ......... 73/862.625 |
| 5,413,611 | A | * | 5/1995 | Haslam et al. ................ 623/25 |
| 5,443,525 | A |   | 8/1995 | Laghi |
| 5,443,528 | A | * | 8/1995 | Allen ........................... 623/52 |
| 5,449,002 | A | * | 9/1995 | Goldman .................... 600/592 |

(Continued)

FOREIGN PATENT DOCUMENTS

EP    0 870 485 A2    10/1988

(Continued)

OTHER PUBLICATIONS

The International Search Report PCT/US03/22330.

(Continued)

*Primary Examiner*—Alvin J. Stewart
(74) *Attorney, Agent, or Firm*—Knobbe Martens Olson & Bear LLP

(57) ABSTRACT

Disclosed is a device and method to aid in the monitoring of the health of an amputee's limb. The device employs a socket preferably including a liner. The liner may be constructed of an inner layer and an outer layer. The inner layer is configured to hold a plurality of sensors able to monitor the physiological health of the enclosed limb. The inner layer further employs a transmission device able to receive data from the sensors and send such data to an end user; the end user being a computer, the amputee, or a doctor. Through receipt of such data, the end user is aided in monitoring the health of the limb.

25 Claims, 6 Drawing Sheets

U.S. PATENT DOCUMENTS

| | | | |
|---|---|---|---|
| 5,468,236 A | | 11/1995 | Everhart et al. |
| 5,569,883 A | * | 10/1996 | Walter et al. .............. 174/84 R |
| 5,619,186 A | * | 4/1997 | Schmidt et al. .......... 340/573.1 |
| 5,728,167 A | * | 3/1998 | Lohmann ...................... 623/36 |
| 5,830,136 A | * | 11/1998 | Delonzor et al. ............ 600/323 |
| 5,840,047 A | * | 11/1998 | Stedham ...................... 600/587 |
| 5,842,982 A | | 12/1998 | Mannheimer |
| 5,888,230 A | * | 3/1999 | Helmy ......................... 623/34 |
| 5,944,661 A | | 8/1999 | Swette et al. |
| 5,971,729 A | | 10/1999 | Kristinsson et al. |
| 5,993,400 A | | 11/1999 | Rincoe et al. |
| 6,030,418 A | * | 2/2000 | Biedermann ................. 623/36 |
| 6,125,291 A | * | 9/2000 | Miesel et al. ............... 600/333 |
| 6,155,120 A | | 12/2000 | Taylor |
| 6,231,616 B1 | * | 5/2001 | Helmy ......................... 623/34 |
| 6,287,253 B1 | | 9/2001 | Ortega et al. |
| 6,500,210 B1 | * | 12/2002 | Sabolich et al. .............. 623/24 |
| 6,560,471 B1 | | 5/2003 | Heller et al. |
| 6,585,774 B2 | * | 7/2003 | Dean et al. ................... 623/37 |
| 6,618,934 B1 | * | 9/2003 | Feldman et al. .............. 29/830 |
| 6,671,531 B2 | * | 12/2003 | Al-Ali et al. ............... 600/344 |
| 6,679,920 B2 | | 1/2004 | Biedermann et al. |
| 6,740,123 B2 | * | 5/2004 | Davalli et al. ................ 623/24 |
| 6,922,592 B2 | * | 7/2005 | Thompson et al. ........... 607/59 |
| 2002/0052663 A1 | | 5/2002 | Herr et al. |
| 2002/0099450 A1 | | 7/2002 | Dean, Jr. et al. |
| 2002/0123673 A1 | * | 9/2002 | Webb et al. ................. 600/300 |
| 2002/0156654 A1 | | 10/2002 | Roe et al. |
| 2002/0183646 A1 | | 12/2002 | Stivoric et al. |
| 2003/0040663 A1 | | 2/2003 | Rule et al. |
| 2003/0078674 A1 | * | 4/2003 | Phillips ....................... 623/37 |
| 2004/0010207 A1 | * | 1/2004 | Flaherty et al. ............. 600/573 |
| 2004/0019288 A1 | * | 1/2004 | Kinast ........................ 600/509 |
| 2004/0167638 A1 | | 8/2004 | Caspers |
| 2006/0047215 A1 | * | 3/2006 | Newman et al. ............ 600/513 |

FOREIGN PATENT DOCUMENTS

| | | |
|---|---|---|
| WO | WO 98/04182 | 2/1998 |
| WO | WO 00/74611 A2 | 12/2000 |

OTHER PUBLICATIONS

Robert M. Havey, et al. "Research Forum—Methodology—Measurements, Part II: Instrumentation and Apparatus," JPO 1996; vol. 8, No. 2, p. 50.

* cited by examiner

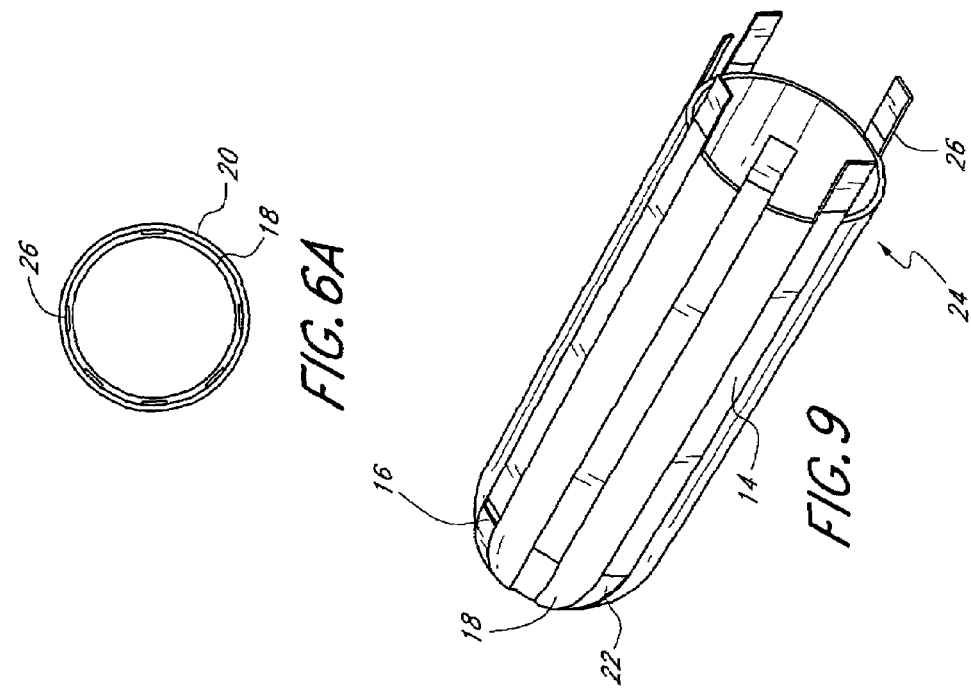
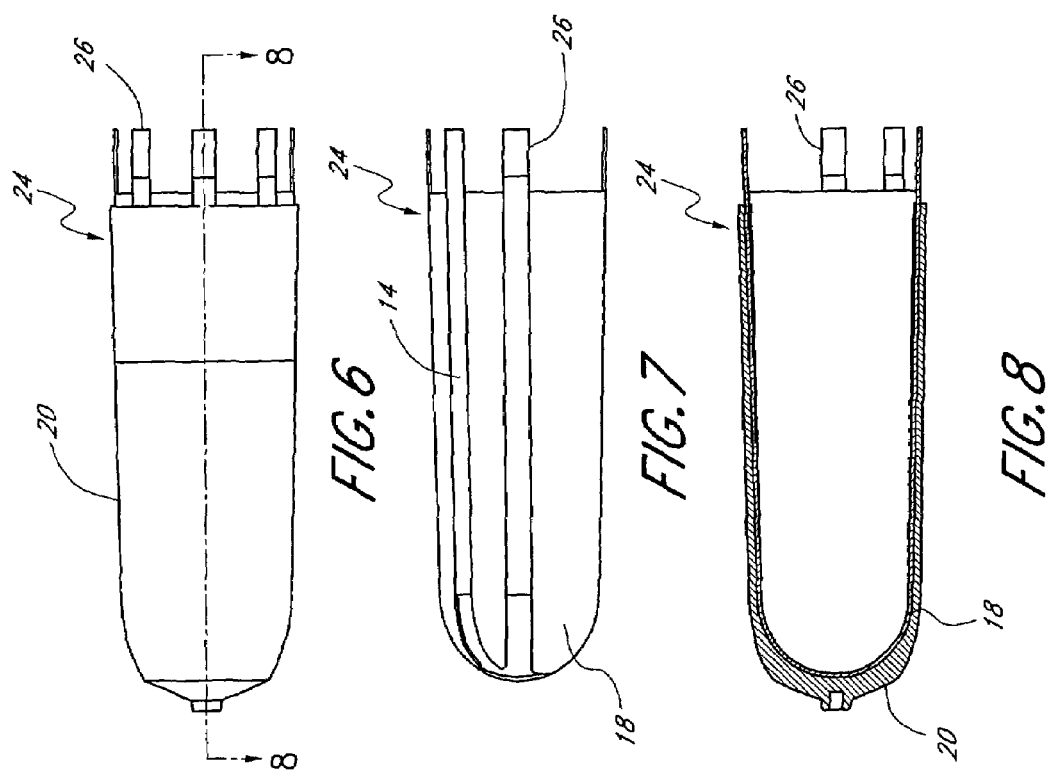

SOCKET LINER INCORPORATING SENSORS TO MONITOR AMPUTEE PROGRESS

PRIORITY INFORMATION

This application claims the priority benefit under 35 U.S.C. § 119(e) of Provisional Application No. 60/394,804 filed Jul. 8, 2002, the entirety of which is hereby incorporated by reference.

BACKGROUND OF THE INVENTION

1. Field of the Invention

The field relates generally to a device and method for monitoring of the health of a person's limbs. More specifically, some embodiments relate to the analysis of data affecting the health of an amputee's limb. Some embodiments are targeted towards monitoring a limb through the use of a socket liner.

2. Description of the Related Art

Through the use of ever improving technology, amputees are finding more ways to function through the use of prosthetic devices. Often an amputee uses a socket placed over a limb which is thereby attached to the prosthetic device. The prosthesis may function as a leg, arm, foot, or hand for the amputee.

Use of sockets, however, may cause irritation, volumetric shrinkage and other adverse reactions to the user. Often liners, socks, sleeves, and other limb coverings are used to aid in the prevention of injury to the limb while the socket is in place. Damage to the limb may still occur despite the protection that a liner may provide.

There exists a need for new devices and methods that provide additional functionality to an amputee who uses a socket.

SUMMARY OF THE INVENTION

Briefly stated, embodiments of the present invention provide a device and method that allows an amputee or a person such as a doctor or prosthetist to monitor various characteristics of a limb. More specifically, the monitoring occurs when the limb is covered by a garment such as a socket or other item having a receiving portion adapted to receive the limb. Preferably, the limb is covered with a socket liner. Optionally the liner may be of a single or multiple layer construction. The liner is configured to hold sensors such as physiological sensors adapted to receive data from the limb throughout the day. The sensors may be constructed to receive a variety of physiological traits from the limb. Preferably, the liner further comprises a transmitter configured to receive data from the sensors and transmit such data to a computer, a user, a doctor or a prosthetist. The receiver of the data is thereby aided in monitoring the health of the enclosed limb.

Accordingly, in one embodiment, a socket is provided for receiving a limb of an amputee. The socket comprises a liner adapted to receive a limb of an amputee, and one or more sensors provided in the liner, the sensors being adapted to monitor physiological data received therein. In one embodiment the liner includes a plurality of grooves for receiving the sensors. The sensors in one embodiment are strips provided along a surface of the liner. In other embodiments, the sensors may be composed of various shapes and sizes. For example, ring-like sensors could be placed around or within the liner. Also, smaller sensors could be placed at discreet locations along the length of the liner. These smaller sensors may be composed of circular or other geometric shapes. In one embodiment the liner is made from two parts adhered together.

One embodiment of a socket liner includes a liner and one or more sensors provided in the liner adapted to monitor data. One liner includes an inner layer, an outer layer, and a sensor in a channel used to monitor physiological characteristics of a limb. Another liner holds a physiological sensor for receiving data from a limb and transmitter for sending the data to a receiver. Another embodiment discloses a garment with a receiving portion to hold a plurality of sensors wherein the garment is configured to transmit received data to an end user. Also provided is a method of monitoring the physiological characteristics of a limb by using data accumulated from a liner having one physiological sensor located therein.

BRIEF SUMMARY OF THE DRAWINGS

FIG. 6 is a side view of a two-layered liner.

FIG. 6a is a top end view of the liner of FIG. 6.

FIG. 7 is a side view of an inner layer with sensors.

FIG. 8 is a cross-sectional view of a two-layered liner.

FIG. 9 is an isometric view of an inner layer with pressure sensors.

DETAILED DESCRIPTION OF THE PREFERRED EMBODIMENTS

Figure 1:
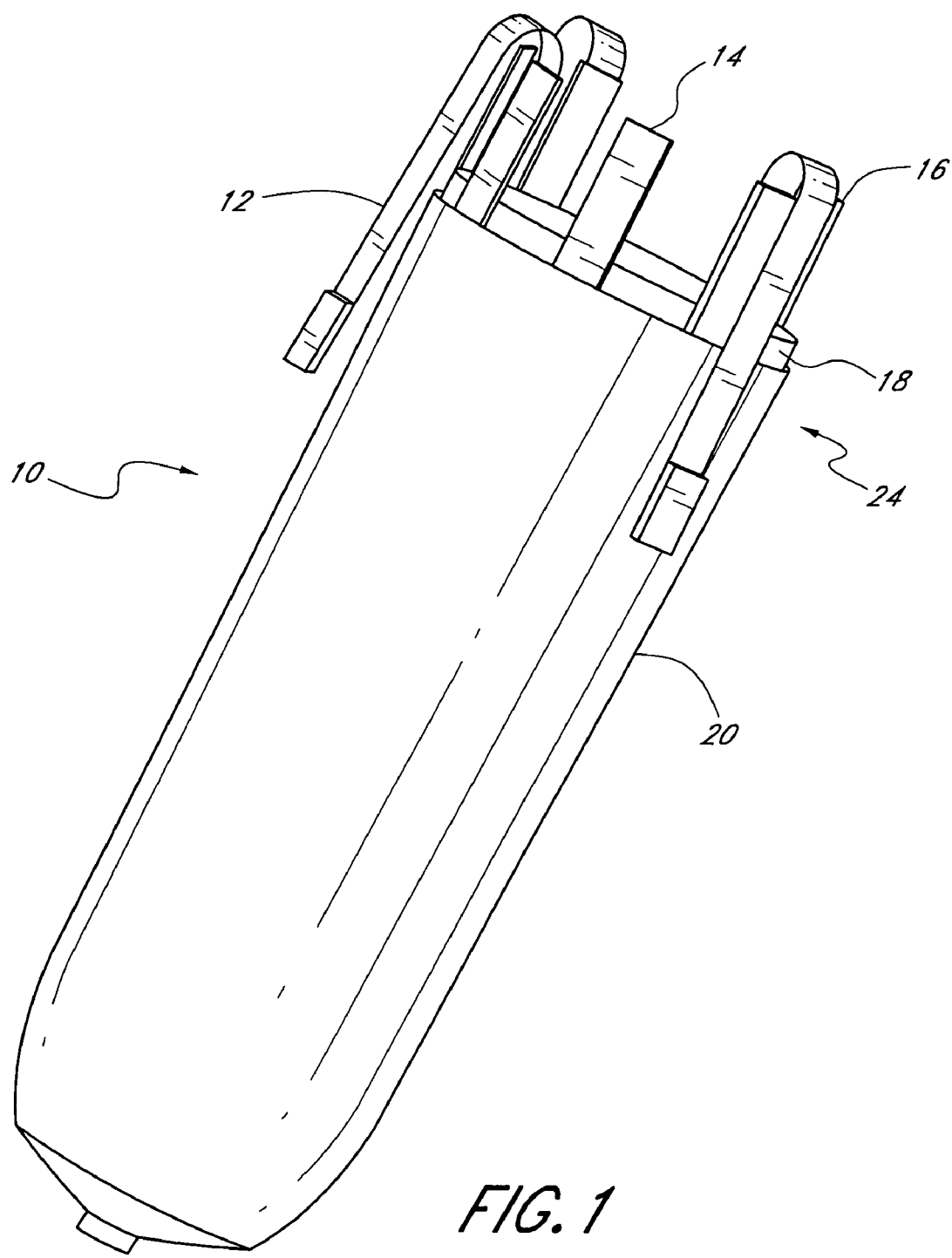
FIG. 1 depicts an assembled embodiment of a two-layered socket liner.

Preferred embodiments of the present invention are directed to developing an interface for amputees, where physical data for a limb can be gathered over a period of time in normal action. In one embodiment a socket is used as an interface between the limb and a prosthesis. Amputees may use liners to provide suspension and comfort inside of the socket. A liner may be made of silicone or other material and may provide a locking mechanism with the socket. Locking liners incorporate a pin and are relied upon for suspension of the socket. Non-locking liners or cushion liners are generally used for comfort purposes and use belts or other mechanisms to provide suspension of the socket. The term liner is meant to be construed as a broad term and may encompass a sock, a sleeve, an insert or other coverings placed over an amputee's limb. At the same time, liner is meant to be used in its plain and ordinary meaning. In one embodiment, described further below, sensors are incorporated into the socket liner that is placed between the limb and the socket. In alternative embodiments, sensors may be incorporated into a socket sock or in the socket itself. Typically socks provide cushioning for the limb and add volume to the limb that is lost throughout the day.

Preferably, sensors are placed in a silicone or other polymer material (e.g., thermoplastic elastomers or polyurethane) that comprise the socket liner. Sensors may include, but are not limited to:

Oxygen sensors for the measurement and mapping of peripheral oxygen, such as by means of an array of high sensitivity Spo2 sensors;

Pressure sensors detecting the fit of the liner and/or socket over the limb;

Temperature sensors;

Sensors to measure blood pressure;

Humidity sensors;

Sensors to measure glucose;

Sensors to measure limb movement within the liner and/or socket throughout the gait;

Sensors to measure volume fluctuation of the limb throughout the day;

Sensors to measure body fat;

Activity monitoring sensors, i.e. how long the prosthesis is worn from day to day and whether there are high periods of activity.

Sensors to measure the shear forces exerted on a limb by the liner and/or socket.

It will be appreciated that other sensors may be used in the liner for different applications and for other diagnostic or physiological measurements.

Data obtained by the sensors can be sent to a remote location to a rehabilitation doctor and/or a CPO (Certified Prosthetist/Orthotist) using telecommunications equipment incorporated into or with the liner. This approach assists amputees to integrate into the society and maximize the comfort and use of their prosthesis. Another objective is to gather medical information about amputees in a statistical way, thus giving possibilities for better treatment. The sensors may be held in place within the liner through the use of grooves, channels, or pockets. The pockets may have opened or closed ends. Alternatively, a combination of grooves, channels, and pockets may exist. Further, the sensors may extend over the liner. The sensors may be made of rigid, soft, or a combination of rigid and soft materials.

Two ways that sensors can be incorporated into a socket liner are integrated sensors, and sensors placed in-between layers of the socket liner. Sensors, however may be placed into socks, socket inserts, the socket itself, as well as other layers of material that may be incorporated into a device placed over an amputee's limb.

FIG. 1 illustrates one embodiment of a socket liner incorporating physiological sensors, more preferably pressure sensors 14, 16 and oxygen sensors 12. The term "physiological sensor" is meant to define a broad term as well as its ordinary meaning. Physiological sensors may be used to measure peripheral oxygen, temperature, humidity, body fat, blood gasses, blood pressure, blood glucose levels, and other related data such as described above. Physiological pressure sensors 14, 16 may be used to monitor the pressure exerted by the limb onto the liner which can be used as a measure of a patient's health. The pressure sensors 14, 16 may also monitor the pressure exerted by the liner 10 and/or socket on the limb. Oxygen sensors 12 may be used to measure peripheral oxygen such as described above.

The liner 10 may comprise a single or multiple layers. Preferably the liner 10 is made in two layers 18, 20. In one embodiment, the inner layer 18 preferably includes up to six longitudinal grooves or channels 22 that the sensors 12, 14, 16 are placed in. Sensors 12, 14, 16 may be placed in one or more of the grooves 22. Once the sensors 12, 14, 16 have been correctly positioned, the outer layer 20 is positioned over the inner layer 18. Next, the inner 18 and outer layers 20 are adhered together. Both parts are preferably made of silicone, although other suitable materials may be used as well.

Figure 2:
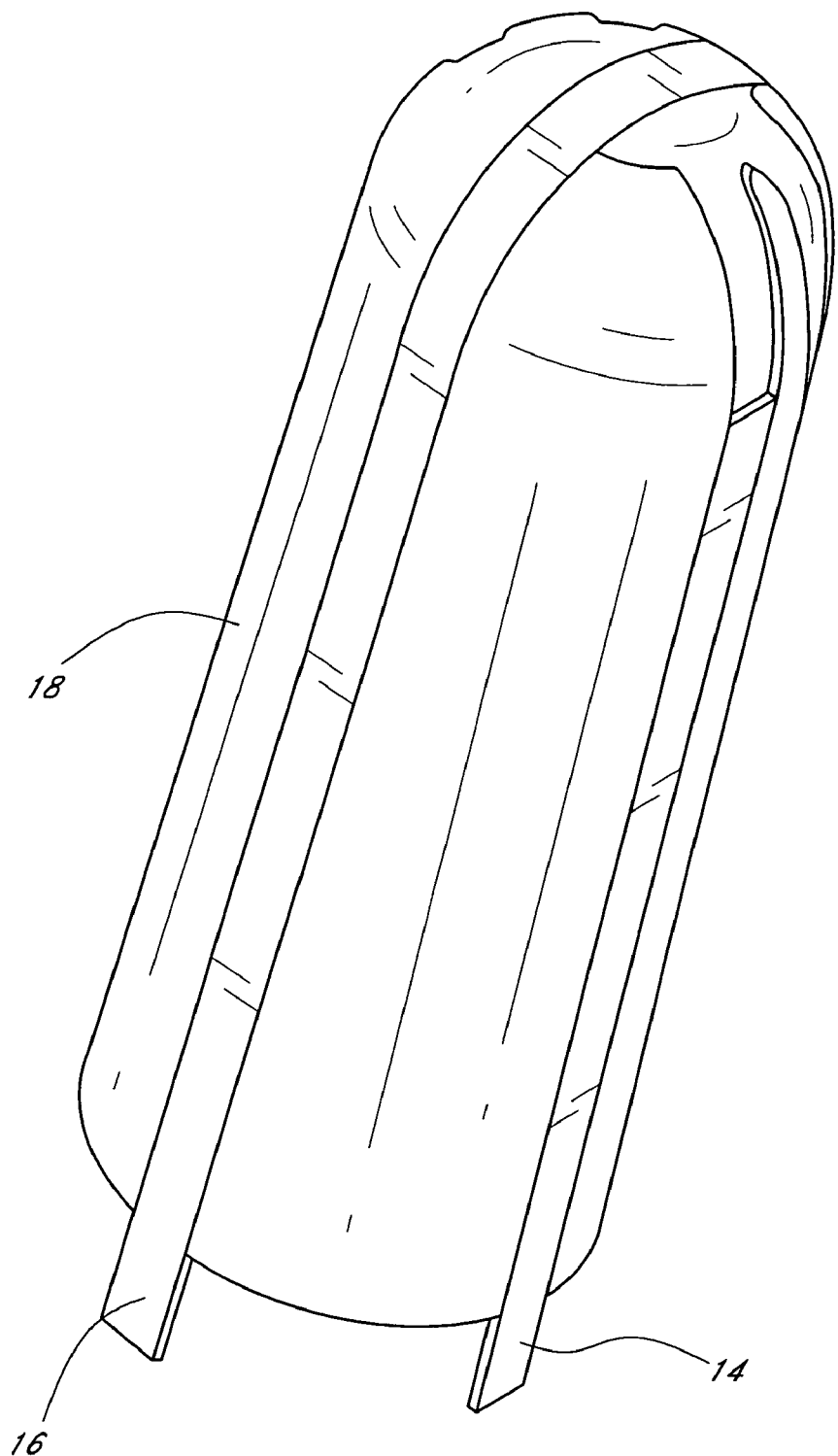
FIG. 2 shows an inner liner with a pressure sensor wrapping over its bottom layer.
Figure 3:
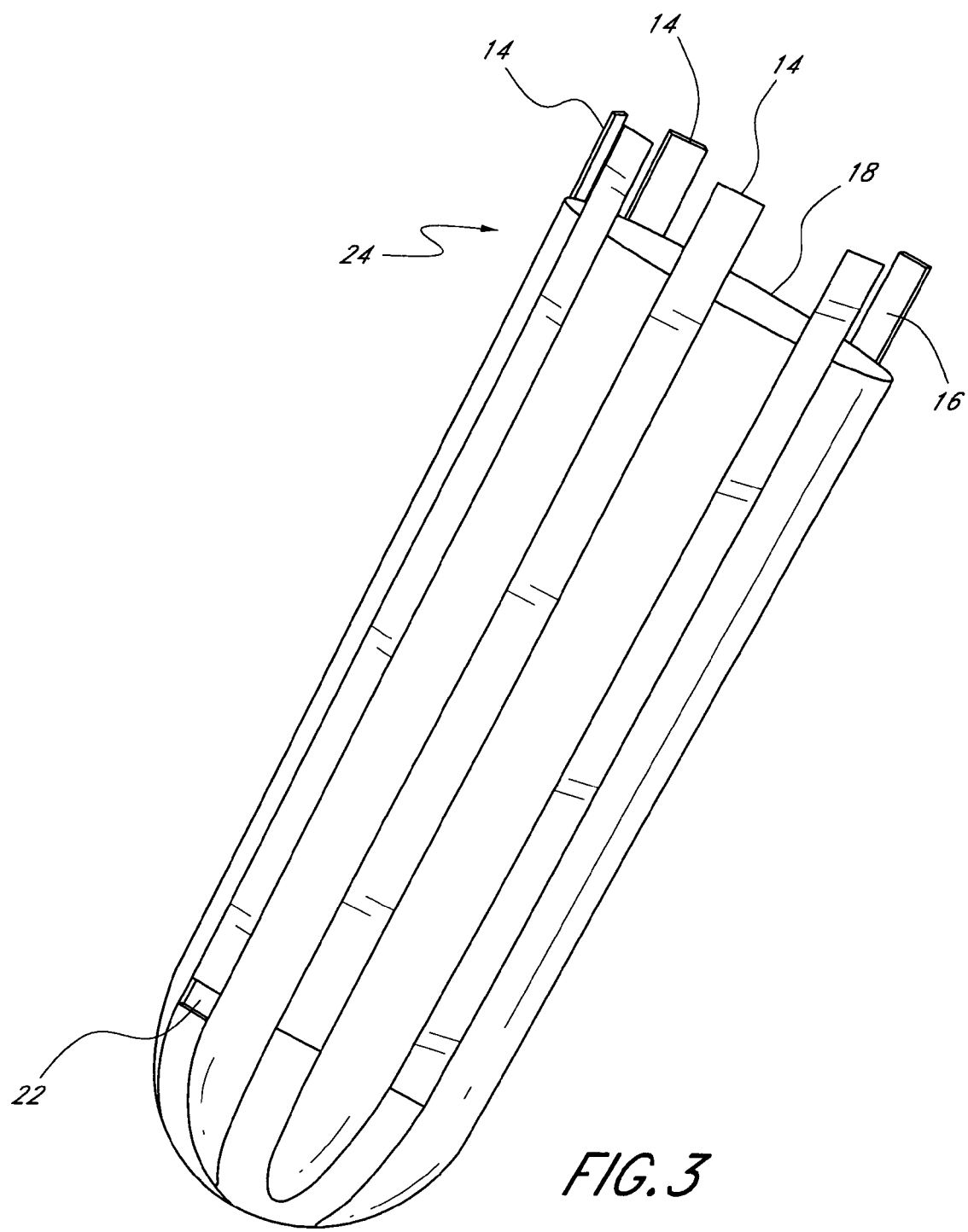
FIG. 3 depicts an alternative view of the inner liner of FIG. 2.

FIGS. 2 and 3 illustrate the inner layer 18 of the liner 10 with six pressure sensors 14, 16 provided therein. As shown in greater detail in FIGS. 6-9, in one embodiment there are provided five short pressure sensors 14, and one long pressure sensor 16. The five short pressure sensors 14 are preferably provided about 45° apart along the circumference of the liner 10, with the one long pressure sensor 16 being positioned 180° opposite the centralmost of the five short sensors 14. In an example where a 300 mm long silicone liner 10 is used, the short sensors 14 are preferably about 260 mm long, and the one long sensor 16 is about 410 mm long, wrapping around the bottom of the inner layer 18 to the opposite side. These lengths provided above refer to the total length of the flexible part of the respective sensor 14, 16. The sensors 14, 16 preferably further include a rigid part 26, located above the upper edge 24 of the liner 10 (as shown in FIGS. 6-9). Any portion of the sensors may be constructed of soft or rigid materials. The sensors may be constructed of silicone and other similar polymer materials. In one embodiment the sensors may be made of a metal and foam combination. In the illustrated embodiment, the rigid part 26 is preferably about 30 mm long.

Figure 4:
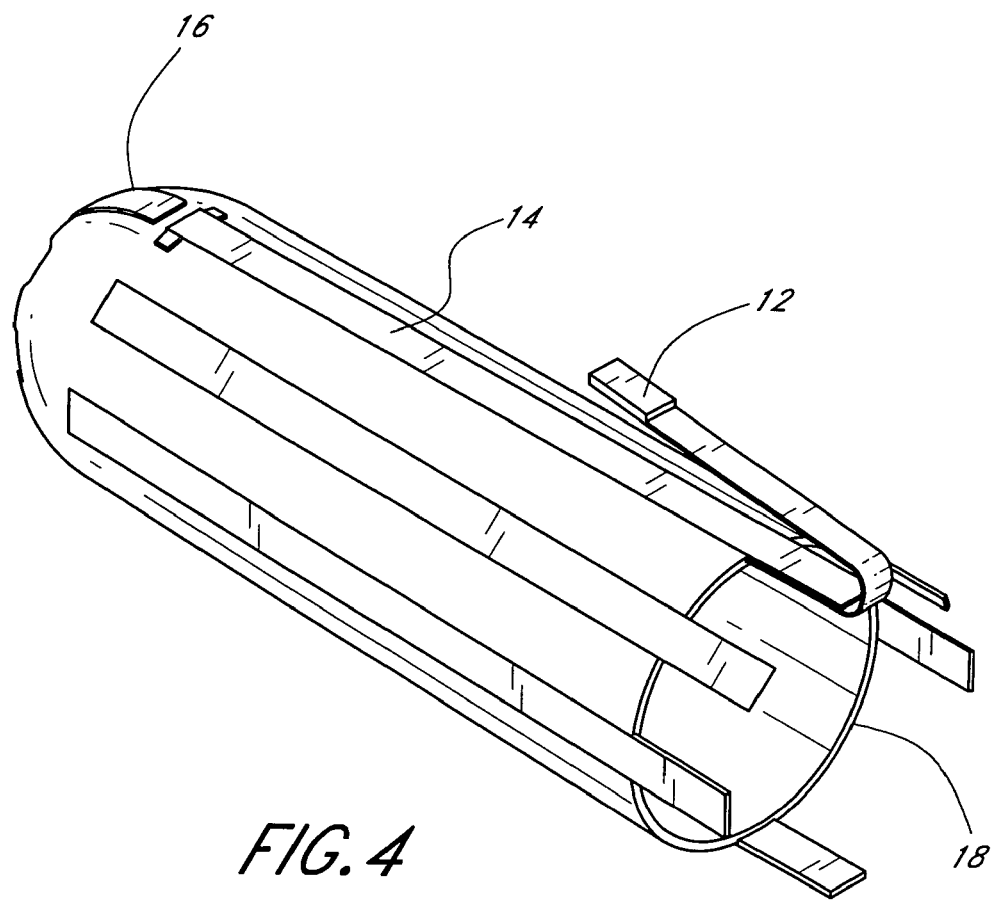
FIG. 4 shows an embodiment of an inner layer of a socket liner having an oxygen sensor and pressure sensors.
Figure 5:
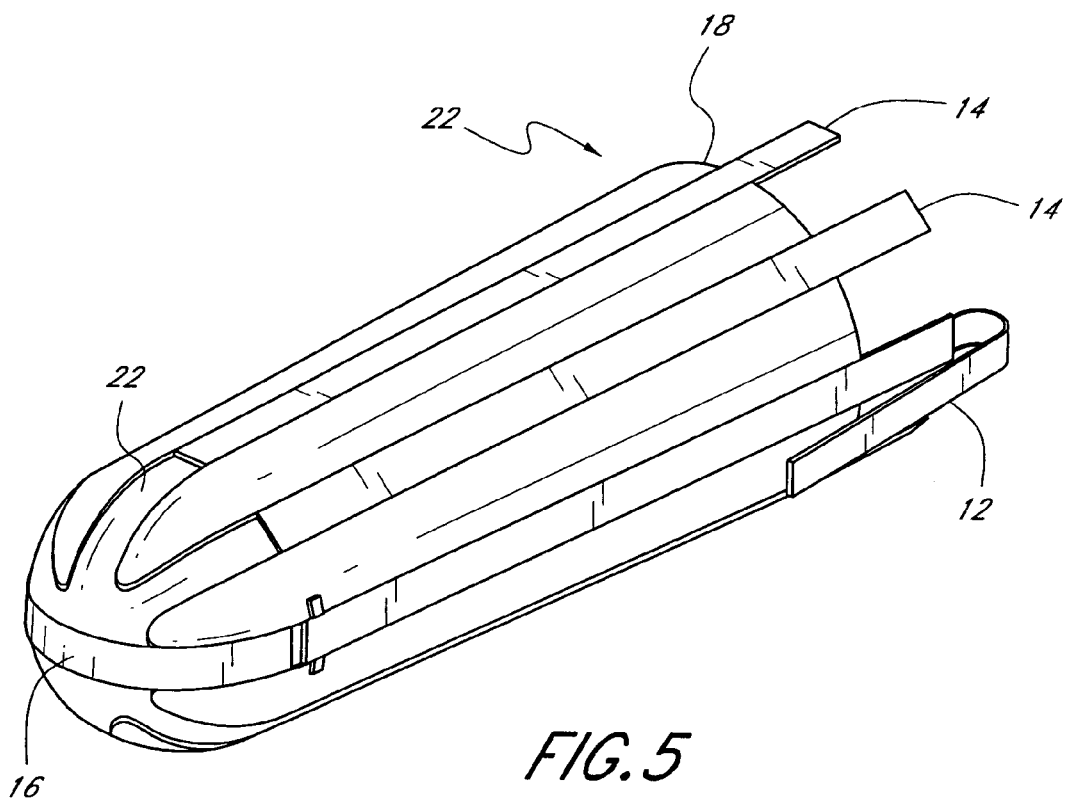
FIG. 5 depicts an alternative view of the socket liner of FIG. 4.

FIGS. 4 and 5 illustrate the inner layer 18 of the liner provided with an oxygen sensor 12 therein. The oxygen sensor 12 may be positioned in a variety of positions including next to, under or extending over the pressure sensors 14, 16. As illustrated in FIGS. 4 and 5, an oxygen sensor 12 is provided over a pressure sensor 14, and both the oxygen sensor 12 and pressure sensors 14, 16 extend over the edge 24 of the liner 10. In another embodiment (not shown), the sensors 12, 14, 16 are completely positioned between the inner 18 and outer layers 20 of the liner 10. In another embodiment, the oxygen sensors 12 are incorporated into the liner 10 without being connected to a pressure sensor 14, 16. Alternatively, oxygen sensors 12 may be incorporated into a liner 10, sock, insert, and/or socket in combination with any of the previously mentioned physiological sensors 12, 14, 16 or by themselves. As illustrated in FIG. 1, in one embodiment of an assembled liner 10, three oxygen sensors 12 are provided in the liner 10.

It will be appreciated that the number and arrangement of sensors 12, 14, 16 in the liner 10 can be varied. It will also be appreciated that other ways of incorporating the sensors 12, 14, 16 into the liner 10 can be used as well. Furthermore, sensors 12, 14, 16 need not be positioned in the liner 10 and may be positioned in the socket itself. Other variations of the described device are also contemplated. Thus, the scope of this invention is not to be limited to the preferred embodiments described above.

What is claimed is:

1. A socket liner for receiving a limb of an amputee, the socket liner comprising:

a liner in the shape of a tubular body having a longitudinal axis that extends from a closed distal end of the liner to an open proximal end of the liner, wherein:

the liner is generally symmetrical about the longitudinal axis, the liner has an inner and an outer layer, and the outer layer serves to provide an interface between the inner layer and a socket; and a physiological sensor configured to receive data from a limb regarding its physiological characteristics;

the sensor being positioned in a channel formed between the liner inner layer and the liner outer layer;

the sensor including an extending portion that extends outwardly from the open proximal end of the liner in a generally longitudinal direction;

the sensor being in communication with a transmitter; and the transmitter configured to send data to a receiver to allow an end user to analyze the physiological characteristics of the limb.

2. The socket liner of claim 1, wherein the sensor wraps around the inner layer.

3. The socket liner of claim 1, wherein the extending portion of the sensor is more rigid than other portions of the sensor.

4. The socket liner of claim 1, further comprising a short sensor that is positioned in a second channel formed between the liner inner layer and the liner outer layer, wherein the short sensor does not extend from the open proximal end of the liner.

5. A socket liner for receiving an amputated limb of an amputee, the socket liner comprising:

an inner liner layer having an interior surface and an exterior surface and having a generally sock-like or sleeve-like configuration to receive, on the interior surface, the amputated limb;

an outer liner layer having an interior surface and an exterior surface and having a configuration generally matching that of the inner liner layer, the exterior surface of the outer liner layer receiving a socket; and at least one sensor configured to receive data from the amputated limb regarding its physiological characteristics, the sensor disposed between the exterior surface of the inner liner layer and the interior surface of the outer liner layer, wherein the sensor is disposed in a channel formed between the exterior surface of the inner liner layer and the interior surface of the outer liner layer, and wherein the sensor includes an extending portion that extends outward from an inner liner layer opening in a generally longitudinal direction.

6. The socket liner of claim 5, wherein the sensor is positioned along a first side of the inner liner layer, around a bottom portion of the inner liner layer, and along a second side of the inner liner layer, the second side of the inner liner layer being opposite the first side of the inner liner layer.

7. A socket liner for receiving an amputated limb of an amputee, the socket liner comprising:

a liner body having a generally sock-like or sleeve-like configuration and having an interior surface and an exterior surface;

the interior surface configured to receive the amputated limb;

the exterior surface having a configuration generally matching that of the interior surface and configured to receive a socket; and a plurality of sensors configured to receive data from the amputated limb regarding its physiological characteristics, the sensor disposed between the exterior surface of the liner body and the interior surface of the liner body, and wherein the sensors comprise elongate strips positioned along a longitudinal axis of the liner body and disposed substantially around a circumference of the liner body.

8. The socket liner of claim 5 or 7, wherein the sensor is an oxygen sensor.

9. The socket liner of claim 5 or 7, wherein the sensor is a pressure sensor.

10. The socket liner of claim 7, wherein the sensor wraps around a bottom portion of the interior surface of the liner body.

11. The socket liner of claim 7, wherein the sensor is molded into the liner body between the liner body interior surface and the liner body exterior surface.

12. The socket liner of claim 7, wherein the sensor includes an extending portion that extends outward form a liner body opening.

13. An apparatus comprising:

an inner liner configured to receive a residual limb of an amputee, wherein the inner liner has the shape of a tubular body with a longitudinal axis that extends from a closed distal end of the inner liner to an open proximal end of the inner liner, and wherein the inner liner is generally symmetrical about the longitudinal axis;

an outer liner positionable over the inner liner to define a liner body, the outer liner having an exterior surface configured to receive a socket thereover, such that the outer liner forms an interface between the inner liner and the socket; and a plurality of sensors configured to receive physiological data from the residual limb, the sensors comprising elongate strips positioned along a longitudinal axis of the liner body and disposed substantially around a circumference of the liner body.

14. The apparatus of claim 13, wherein the sensor is an elongate strip configured to be wrapped around a portion of the inner liner.

15. The apparatus of claim 13, further comprising a plurality of sensors configured to receive physiological data from the residual limb.

16. The apparatus of claim 13, further comprising an adhesive disposed between the inner liner and the outer liner.

17. The apparatus of claim 13, further comprising a transmitter configured to send data to a receiver to allow an end user to analyze physiological characteristics of the residual limb.

18. The apparatus of claim 13, wherein the sensor is selected from the group consisting of an oxygen sensor and a pressure sensor.

19. An apparatus for monitoring amputee progress, comprising:

a liner having an inner layer and an outer layer, wherein the liner inner layer is configured to receive a residual limb of an amputee, the outer layer being coupleable with a socket;

a plurality of sensors, each sensor being formed as an elongate strip and being able to sense physiological characteristics of the residual limb along substantially its entire length, the sensors being disposed between the inner liner layer and outer liner layer such that the two layers are substantially laminated to each other, the elongate sensors being disposed longitudinally along the body of the liner substantially about the circumference of the liner; and a transmitter configured to send data to a receiver to allow an end user to analyze the physiological characteristics of the residual limb.

20. The apparatus of claim 19, wherein the sensors are in a channel formed in one layer such that the other layer is laminated to that layer except where the sensor is located.

21. The apparatus of claim 19, wherein the sensors are integrated into a wall of the liner.

22. The apparatus of claim 19, wherein at least one sensor extends along a closed distal end of the liner to correspond to the distal end of the residual limb.

23. The apparatus of claim 19, wherein at least one of the sensors is selected from the group consisting of an oxygen sensor and a pressure sensor.

24. The apparatus of claim 19, further comprising a supplementary physiological sensor incorporated into the socket.

25. The apparatus of claim 19, wherein at lease one of the elongate strips has a portion folded back onto itself.

* * * * *

UNITED STATES PATENT AND TRADEMARK OFFICE
CERTIFICATE OF CORRECTION

| | |
|---|---|
| PATENT NO. | : 7,377,944 B2 |
| APPLICATION NO. | : 10/615336 |
| DATED | : May 27, 2008 |
| INVENTOR(S) | : Janusson et al. |

It is certified that error appears in the above-identified patent and that said Letters Patent is hereby corrected as shown below:

In Column 6, Line 5, delete "form" and insert -- from --, therefor.

In Column 8, Line 4, delete "at lease" and insert -- at least --, therefor.

Signed and Sealed this

Twenty-sixth Day of May, 2009

JOHN DOLL
*Acting Director of the United States Patent and Trademark Office*